(12) United States Patent
Elkins

(10) Patent No.: US 6,340,023 B2
(45) Date of Patent: Jan. 22, 2002

(54) REBREATHER NEBULIZER DEVICE

(76) Inventor: John I. Elkins, 151 Montclair Ave., St. James, NY (US) 11780

( * ) Notice: Subject to any disclaimer, the term of this patent is extended or adjusted under 35 U.S.C. 154(b) by 0 days.

(21) Appl. No.: 09/737,162

(22) Filed: Dec. 14, 2000

Related U.S. Application Data
(60) Provisional application No. 60/204,953, filed on May 17, 2000.

(51) Int. Cl.$^7$ ............................................... A61M 11/00
(52) U.S. Cl. ............................. 128/200.21; 128/200.19; 128/200.22; 128/203.12; 128/203.14; 128/203.28; 128/203.29; 128/204.28; 128/205.13; 128/205.17
(58) Field of Search ........................ 128/200.21, 203.12, 128/200.14, 203.28, 203.29, 205.13, 205.17, 203.14, 204.28, 200.22

(56) References Cited

U.S. PATENT DOCUMENTS

| | | |
|---|---|---|
| 3,667,463 A | 6/1972 | Barnes |
| 3,769,973 A | 11/1973 | Esbenshade, Jr. |
| 4,865,027 A | 9/1989 | Laanen et al. |
| 4,886,055 A | 12/1989 | Hoppough |
| 5,277,175 A | 1/1994 | Riggs et al. |
| 5,586,551 A | 12/1996 | Hilliard |
| 5,701,886 A | 12/1997 | Ryatt |

*Primary Examiner*—John G. Weiss
*Assistant Examiner*—Darwin P. Erezo
(74) *Attorney, Agent, or Firm*—Greensfelder, Hemker & Gale, P.C.

(57) ABSTRACT

An apparatus for delivering a highly concentrated mixture of aerosolized liquid and pressurized gas to a patient including a collapsible membrane defining a chamber, the membrane further defining a first opening and a second opening in communication with the chamber. A mask defining an enclosure having a first passageway in communication with the first opening. A nebulizer having a body defining a reservoir for holding the liquid therein, the body including an inlet orifice and an outlet orifice which communicates with the second opening. A pressurized gas source which contains a pressurized gas with the pressurized gas source being in communication with the inlet orifice for providing the pressurized gas to the nebulizer. When the pressurized gas from the pressurized gas source enters the nebulizer, the pressurized gas mixes to form a mixture with the liquid inside the reservoir of the nebulizer. The mixture is then forced from the reservoir to the chamber before freely communicating in either direction between the chamber and the mask.

11 Claims, 4 Drawing Sheets

REBREATHER NEBULIZER DEVICE

CROSS-REFERENCE TO RELATED APPLICATIONS

This application is based upon Provisional Patent Application, Serial No. 60/204,953, entitled "Integrated Respiratory/Ventilation System For Improved Patient Care", filed May 17, 2000, the contents of which are incorporated herein by reference in their entirety and continued preservation of which is requested.

BACKGROUND OF THE INVENTION

1. Field of the Invention

The present invention relates to rebreather nebulizer devices, and more particularly to rebreather nebulizer devices which simultaneously provide highly concentrated levels of aerosolized liquid and pressurized gas. More specifically, the present invention relates to rebreather nebulizer devices that simultaneously provide highly concentrated levels of aerosolized liquid and pressurized gas while ensuring more effective operation of the nebulizer.

2. Prior Art

Patients suffering from a number of severe respiratory conditions may require elevated levels of oxygen and/or respiratory therapy in which a medicant is inhaled by the patient using a nebulizer. Equipment well known in the art, such as a Gin nebulizer, can deliver up to one hundred percent oxygen to a patient in order to meet the patient's respiratory demands. In fact, oxygen flow rates of up to eighty liters per minute may be delivered to the patient by these systems.

Drug nebulizers may also be used to provide therapy to patients having severe respiratory illnesses. Typically, drug nebulizers include a bowl in which a liquid medicant is placed and aerosolized using a pressurized flow of gas. Utilizing the Bernoulli principle, liquid is drawn through an aspirator tube into the path of a high velocity pressurized gas which renders the liquid into a fine mist. Inertial forces then cause the mist to flow out of the nebulizer through a delivery system and to the patient. Nebulized medicant delivery is a preferred method of delivery to a patient because the smaller particles of medicant can be more effectively delivered to a patient's lungs.

However, problems can occur when a doctor orders drug nebulizer treatments for a patient that also requires high concentrations of oxygen because conventional drug nebulizers can only deliver less than half the oxygen required by the patient which would result in an undesirable drop in a patient's blood oxygen level. To avoid endangering the patient, drug nebulizer treatments are provided in-line with high flow oxygen delivery systems. Although such an arrangement maintains the desired blood oxygen levels of the patient, the actual amount of medicant delivered by the drug nebulizer is highly diluted.

U.S. Pat. No. 5,586,551 to Hilliard discloses a non-rebreather oxygen mask in communication with a nebulizer unit wherein oxygen and an aerosolized medicant are separately delivered to the mask through a one-way valve. While the one-way valve prevents the flow of aerosolized medicant and oxygen to a patient during the patient's exhalation, the concentration of aerosolized medicant delivered to the patient is diluted. Moreover, because the nebulizer is not directly in-line with a patient's nasal passageway, the one-way valve reduces the amount and effective delivery of aerosolized medicant to the patient.

Another advancement in the art is found in U.S. Pat. No. 4,865,027 to Laanen et al. which discloses a reservoir bag connected in series to both a drug nebulizer and a mask having an inlet with a one-way valve. The Laanen reference discloses a single oxygen source which simultaneously delivers high concentrations of oxygen and aerosolized medicant through the one-way valve. However, the use of a one-way valve has multiple disadvantages. First, due to the increased amount of oxygen flow through the nebulizer that is required to satisfy a patient's oxygen level needs, the medicant may be "blown out" of the nebulizer bowl, thereby rendering it unavailable for delivery to a patient. Further, the medicant may be delivered too quickly to the patient, which greatly reduces the intended benefits to the patient. Also, the oxygen being delivered to the patient may be forced into a turbulent flow condition due to the heightened pressure fluctuations caused by the one-way valve which adversely affects the size of the aerosolized medicant particles and results in a less effective delivery of the medicant to the patient. In addition to disrupting the flow of aerosolized medicant particles, a portion of these particles may be deposited on the surface of the one-way valve, thereby further decreasing the effectiveness of the nebulizer. Pronounced pressure fluctuations may also dislodge the connection between the pressurized oxygen source and the nebulizer with potentially tragic results.

Therefore, there appears a need in the art for a rebreather nebulizer device that simultaneously provides highly concentrated levels of aerosolized liquid and pressurized gas while additionally ensuring effective unobstructed operation of the nebulizer without the use of valves or the like to control the flow of fluid to the patient.

OBJECTS AND SUMMARY OF THE INVENTION

The primary object of the present invention is to provide a rebreather nebulizer device that simultaneously provides highly concentrated levels of aerosolized liquid and pressurized gas.

Another object of the present invention is to provide a rebreather nebulizer device that simultaneously provides highly concentrated levels of aerosolized liquid and pressurized gas while additionally ensuring effective operation of the nebulizer.

A further object of the present invention is to provide a rebreather nebulizer device that is compatible with conventional nebulizers.

Yet a further object of the present invention is to provide a rebreather nebulizer device that may be used with a second pressurized gas source.

Another further object of the present invention is to provide a rebreather nebulizer device that does not require the use of valves to control the flow of liquid and gas to the patient.

These and other objects of the present invention are realized in the preferred embodiment of the present invention, described by way of example and not by way of limitation, which provides for a rebreather nebulizer device having a novel free flow connection between a mask passageway and collapsible membrane.

In brief summary, the present invention overcomes and substantially alleviates the deficiencies in the prior art by providing an apparatus for delivering a highly concentrated mixture of aerosolized liquid and pressurized gas to a patient. The apparatus comprises a collapsible membrane defining a chamber therein with the membrane further including a first opening and a second opening in communication with the chamber, a mask defining an enclosure having a first passageway in communication with the first opening of the membrane, and a nebulizer having a body defining a reservoir for holding liquid therein with the body including an inlet orifice and an outlet orifice which communicates with the second opening. A pressurized gas source containing a pressurized gas in communication with the inlet orifice of the nebulizer is provided for mixing with the liquid inside the nebulizer. When the pressurized gas from the pressurized gas source enters the nebulizer, the pressurized gas mixes to form a mixture with the liquid inside the reservoir of the nebulizer. The mixture is then forced from the reservoir to the chamber of the membrane before freely communicating in either direction between the chamber and the mask.

Additional objects, advantages and novel features of the invention will be set forth in the description which follows, and will become apparent to those skilled in the art upon examination of the following more detailed description and drawings in which like elements of the invention are similarly numbered throughout.

DETAILED DESCRIPTION OF THE INVENTION

Figure 1:
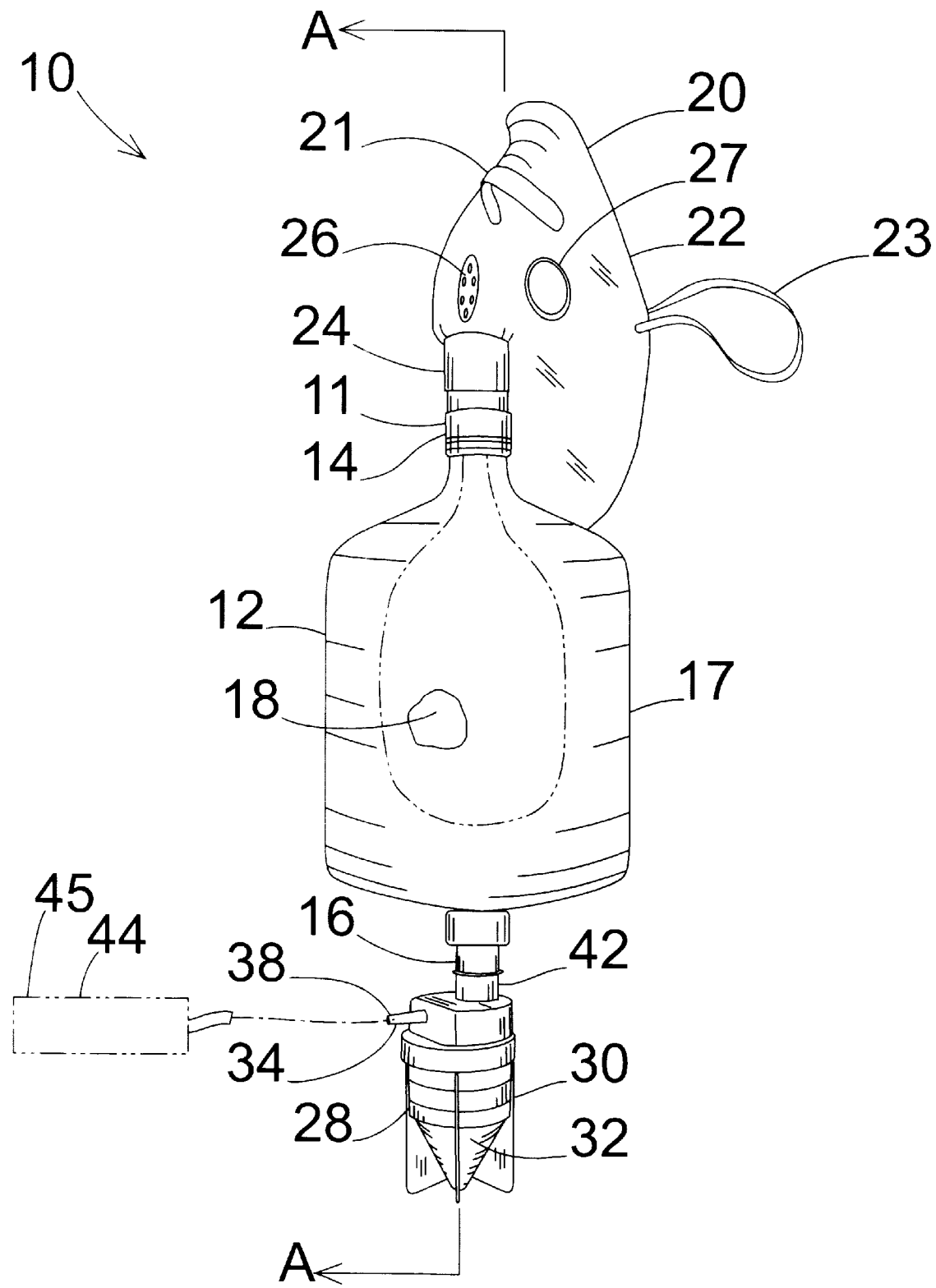
FIG. 1 is a perspective view of a rebreather nebulizer device according to the present invention.

Referring to the drawings, the preferred embodiment of the rebreather nebulizer device of the present invention is illustrated and generally indicated as 10 in FIG. 1. Rebreather nebulizer device 10 comprises a nebulizer 28 containing a liquid 36, a membrane 12 for delivery of a mixture of pressurized gas 45 and liquid 36 to the patient, a mask 20 that delivers the mixture to the patient and vents exhaled air to atmosphere, and a pressurized gas source 44 for providing a pressurized gas 45 to nebulizer 28.

Figure 2:
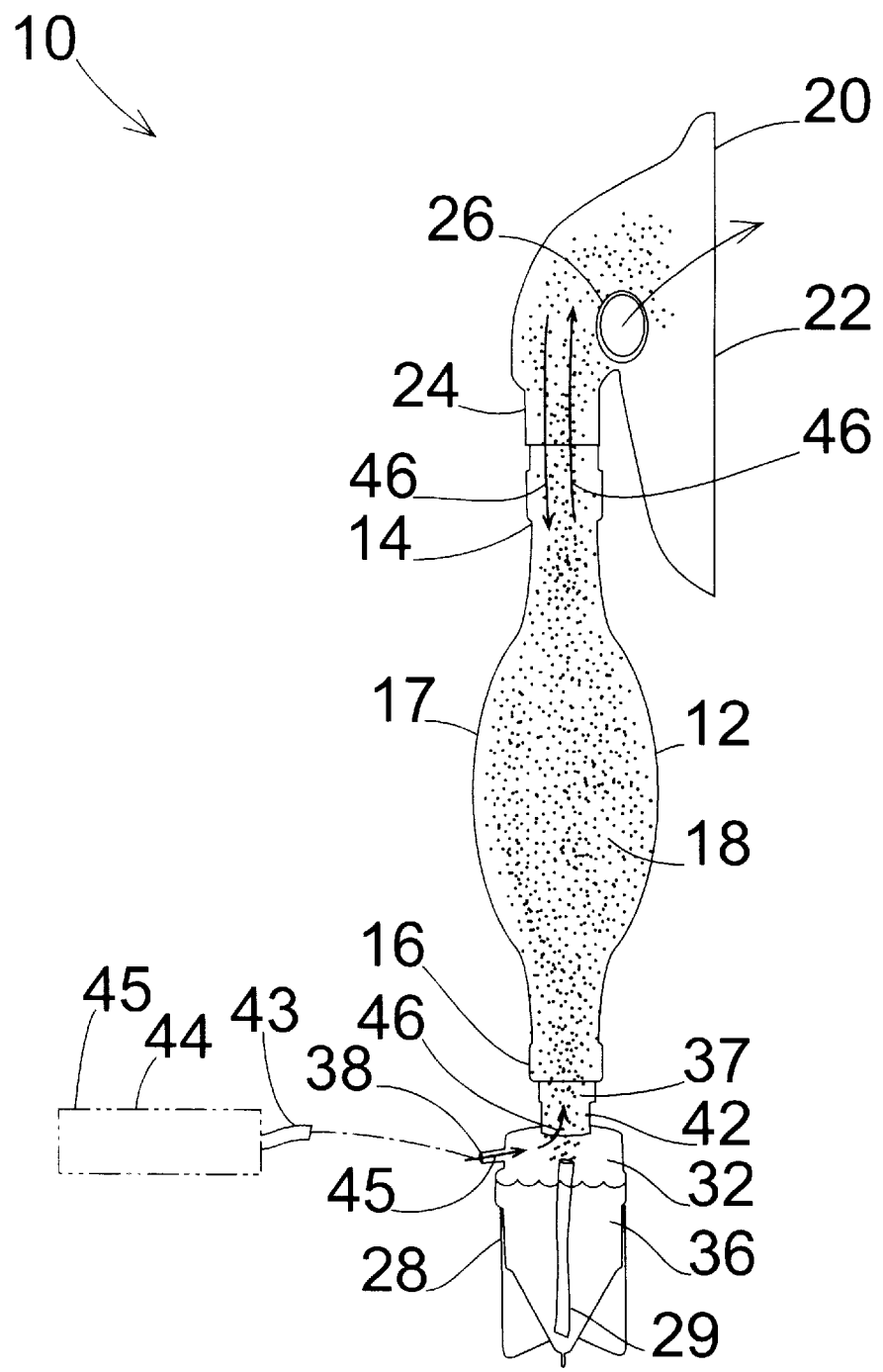
FIG. 2 is a cross sectional view of the a rebreather nebulizer device taken along line A—A of FIG. 1 according to the present invention.

Referring to FIGS. 1 and 2, membrane 12 comprises a collapsible body 17 which is responsive to pressure changes from pressurized gas 45 and a patient's respiratory cycles as shall be discussed in greater detail below. Body 17 defines an internal chamber 18 which includes a first opening 14 and a second opening 16. First opening 14 establishes unrestricted communication with mask 20, while second opening 16 is in unrestricted communication with nebulizer 28.

As further shown, mask 20 includes an enclosure 22 which defines a first passageway 24 for freely communicating with first opening 14 of membrane 12. Additionally, enclosure 22 defines second passageways 26,27 for venting a portion of a patient's exhalation to atmosphere. An elastic strap 23 is provided which is attached to opposing lateral edges of enclosure 22 for securing the periphery of enclosure 22 in fluid tight relationship with the patient's face. As further shown, a pliable clip 21 is provided above first passageway 24 which may be adjustably manipulated to conform to the patient's exterior nasal profile. It will be appreciated by one of ordinary skill in the art that properly adjusting clip 21 improves the patient's comfort level due to clip 21 forming a conformal "fit" with the patient's face, while also maintaining a fluid tight relationship with enclosure 22.

Preferably, nebulizer 28 comprises a body 30 defining a reservoir 32 for holding liquid 36, for example a medicant, therein. Body 30 has an inlet orifice 38 for receiving pressurized gas 45 from a pressurized gas source 44. Secured within reservoir 32 is an aspirator tube 29. Using the Bernoulli principle, pressurized gas 45 which enters inlet orifice 38 draws liquid 36 from aspirator tube 29. Liquid 36 is then exposed to the pressurized gas 45 after passing through aspirator tube 29 and becomes aerosolized liquid 37. As pressurized gas 45 is continually introduced through inlet orifice 38, aerosolized liquid 37 and pressurized gas 45 combine to form a mixture 46. Mixture 46 is then forced by pressurized gas 45 from reservoir 32 through second opening 16 and into chamber 18 of membrane 12. Pressurized gas source 44 is housed in a container, such as a tank, and provides pressurized gas 45, preferably oxygen, to the patient.

According to one aspect of the present invention, chamber 18 of membrane 12 is of a predetermined size such that during a patient's exhalation, approximately the first one-third of the total volume of membrane 12 is exhaled by the patient and freely passes from mask 20 through first passageway 24 and into chamber 18. The remaining volume of the patient's exhalation is vented to atmosphere through second passageway 26. Conversely, during the patient's inhalation a portion of the total volume of chamber 18 freely passes through first passageway 24 into enclosure 22 and breathed in by the patient.

The operation of rebreather nebulizer device 10 shall now be discussed. Referring to FIG. 2, pressurized gas source 44 is connected to inlet connector 34 of nebulizer 28 through a tube 43. After this connection is completed and pressurized source 44 is opened so that it is in communication with tube 43, inlet orifice 38 of nebulizer 28 receives and directs pressurized gas 45 from pressurized gas source 44 into reservoir 32 of nebulizer 28. Utilizing the Bernoulli principle, liquid 36 in reservoir 32 is drawn through aspirator tube 29 and into the path of pressurized gas 45 which renders liquid 36 into a mixture 46 of aerosolized liquid 37 and pressurized gas 45. Pressurized gas 45 then forces mixture 46 from reservoir 32 to chamber 18 of membrane 12. Once chamber 18 begins filling with mixture 46, mask 20 may be secured about a patient's face. As a patient inhales, the mixture 46 freely communicates between chamber 18 and mask 20. This free communication, due to the absence of any valve arrangement noted in the prior art, provides several benefits, including more effective delivery of aerosolized liquid 37 to a patient's lungs by using a portion of the patient's exhalation to supplement the new mixture 46 being delivered to the patient.

The present invention contemplates an unrestricted communication between mask 20 and chamber 18 of membrane 12. As a patient begins to exhale, approximately the first one-third of the total volume of the patient's exhalation freely passes into chamber 18 due to the unrestricted passageway between enclosure 22 and chamber 18. This one-third volume is referred to in the art as dead space. Dead space corresponds to any area of the respiratory tract where no gas exchange occurs with the patient. Thus, this dead space mixture is uncontaminated with carbon dioxide from the patient, and further maintains its original concentration of oxygen and aerosolized liquid 37. By freely permitting the exhaled dead space mixture to return to chamber 18 for rebreathing by the patient during a subsequent inhalation, the flow rate required to sustain a patient is effectively reduced by one-third without any adverse effect to the patient.

This one-third volume savings of required flow rate additionally permits a more effective operation of nebulizer 28. By requiring less pressurized gas 45 to flow through liquid-filled reservoir 32, the level of pressure from pressurized gas source 44 applied to reservoir 32 may be likewise reduced. This reduced pressure prevents liquid 36 which is contained in reservoir 32 from being "blown out" and made otherwise unavailable for use by the patient. Further, the full intended benefit of nebulizer 28 may now be realized because the reduced flow rate of pressurized gas 45 causes liquid 36 to be more slowly aerosolized. In other words, by slowing the rate of aerosolization, liquid 36 can be more controllably dispensed to a patient over a predetermined period of time to derive its maximum intended benefit. An additional benefit is that less pressure is required to achieve the reduced flow of pressurized gas 45. As the pressure level of pressurized gas 45 passing through tube 43 is reduced, the inside diameter of tube 43 is also reduced thereby improving the connection between tube 43 and inlet connector 34 from inadvertent uncoupling.

Figure 3:
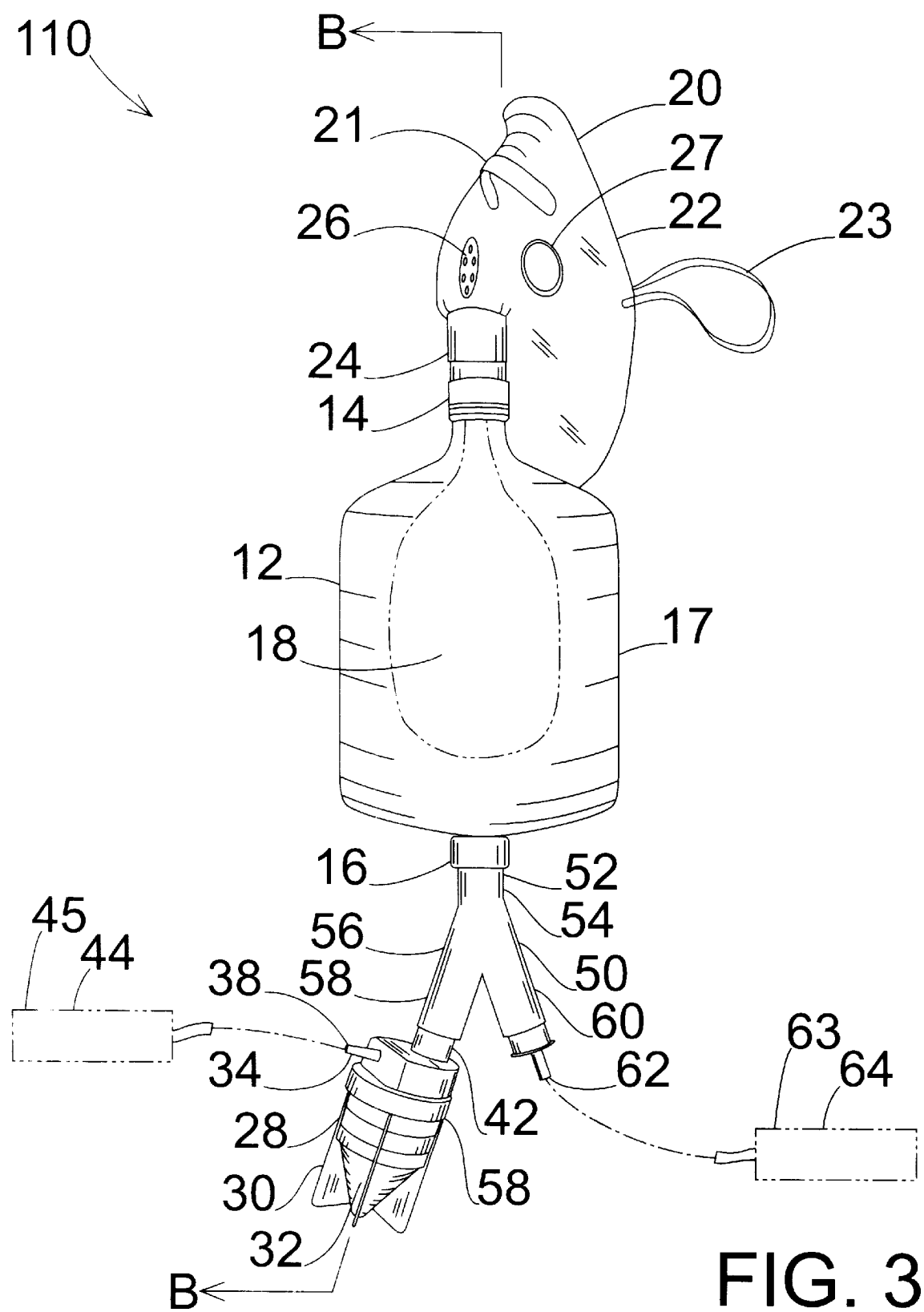
FIG. 3 is a perspective view of an alternative embodiment of the rebreather nebulizer having an additional connector according to the present invention.
Figure 4:
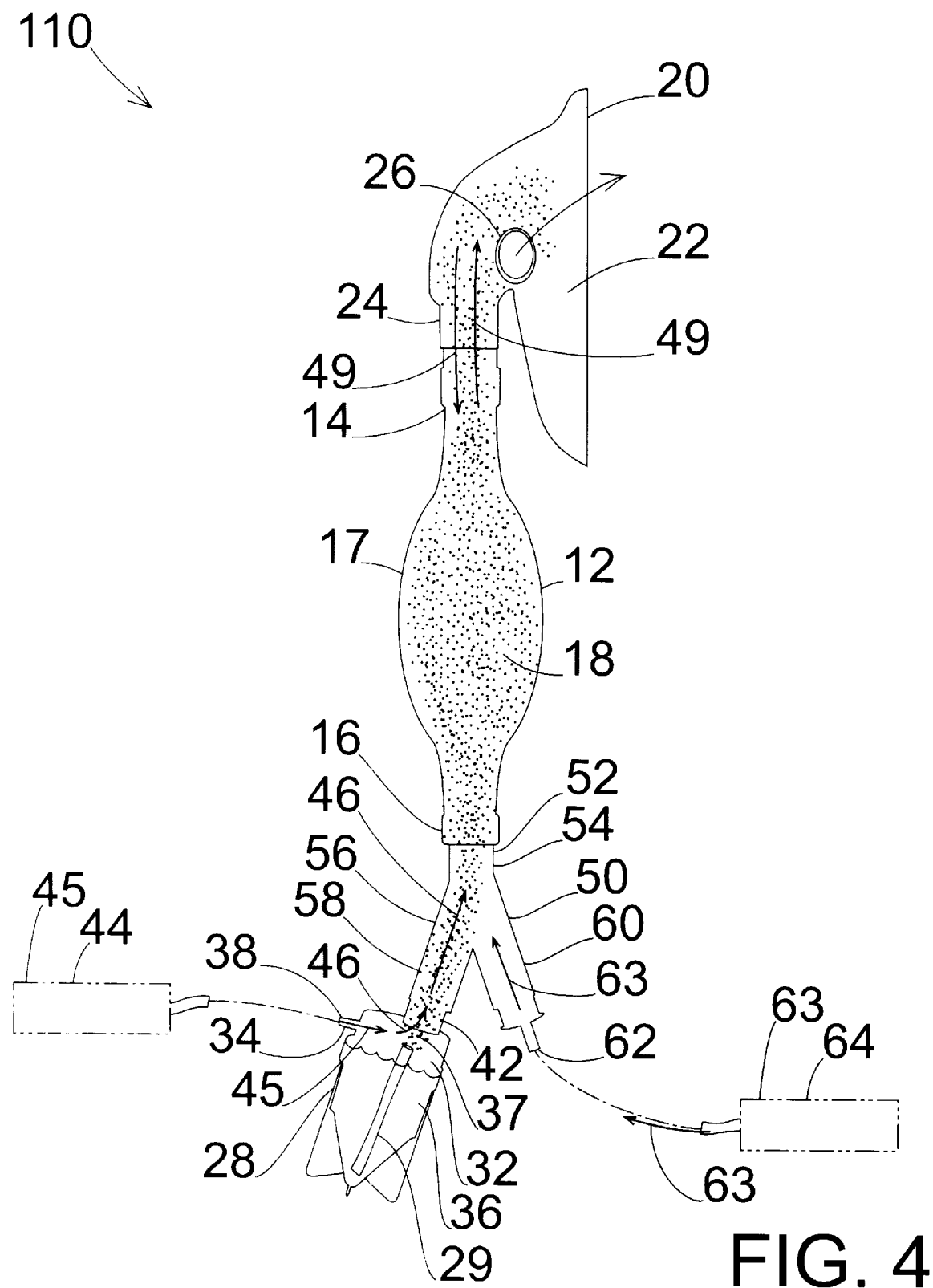
FIG. 4 is a cross sectional view the alternative embodiment taken along line B—B of FIG. 3 according to the present invention.

Referring to FIGS. 3 and 4, an alternate embodiment of rebreather nebulizer device 10 shall now be discussed. As with the preferred embodiment, nebulizer 110 comprises a mask 20, membrane 12 and nebulizer 28 which perform similar functions. However, nebulizer device 110 further comprises a connector 50 which is inserted between outlet orifice 42 of nebulizer 28 and second opening 16 of membrane 12. Connector 50 has an outlet connector 52 defining an outlet aperture 54 for securing in fluid communication with second opening 16. Additionally, connector 50 further includes a first inlet connector 56 defining a first inlet aperture 58 therein for communicating with outlet orifice 42 and a second inlet connector 60 defining a second inlet aperture 62 for communicating with a second pressurized gas source 64. Second pressurized gas source 64 contains a second pressurized gas 63. Moreover, outlet aperture 54, first inlet aperture 58 and second inlet connector 60 are all in fluid communication with one another.

In operation, referring specifically to FIG. 4, second pressurized gas 63 flows through second inlet aperture 62 and into chamber 18. Introduction of pressurized gas 45 into nebulizer 28 and subsequently into chamber 18 operates in a similar manner as in the preferred embodiment. In chamber 18, mixture 46 of aerosolized liquid 37 and pressurized gas 44 from nebulizer 28 is further mixed with second pressurized gas 63. This new mixture 49 is then introduced into enclosure 22 of mask 20 for delivery to the patient.

Preferably, second pressurized gas 63 may be oxygen, in which case the flow rate of pressurized gas 45 through nebulizer 28 may be further reduced if required. Further, second pressurized gas 63 may be a different gas or mixture of gases other than oxygen. For example, a mixture of oxygen and helium may be introduced into second inlet aperture 62. This new mixture permits improved flow of aerosolized liquid 37 for better delivery of mixture 49 to the more restricted areas of a patient's lungs. The applicant has found that such treatments have proven extremely useful for asthmatics with severe bronchspasms. It should be appreciated by one skilled in the art that connector 50 can have any number of additional inlets and be usable with any number of combinations of pressurized gases.

It should be understood from the foregoing that, while particular embodiments of the invention have been illustrated and described, various modifications can be made thereto without departing from the spirit and scope of the present invention. Therefore, it is not intended that the invention be limited by the specification; instead, the scope of the present invention is intended to be limited only by the appended claims.

I claim:

1. An apparatus for delivering a highly concentrated mixture to a patient comprising:

a collapsible membrane defining a chamber therein, said membrane further defining a first opening and a second opening in communication with said chamber;

a mask defining an enclosure having a first passageway in communication with said first opening;

a nebulizer having a body defining a reservoir for holding a liquid therein, said body including an inlet orifice and an outlet orifice, said outlet orifice in communication with said second opening of said membrane;

a pressurized gas source containing a pressurized gas, said pressurized gas source in communication with said inlet orifice for providing said pressurized gas to said nebulizer;

wherein when said pressurized gas from said pressurized gas source enters said nebulizer, said pressurized gas mixes to form a mixture with said liquid inside said reservoir of said nebulizer, wherein said mixture is forced from said reservoir to said chamber before freely communicating in either direction between said chamber and said mask.

2. An apparatus according to claim 1 wherein said enclosure further defining at least one second passageway for permitting a patient to vent to atmosphere.

3. An apparatus according to claim 1 wherein a portion of a patient's exhalation returns to said collapsible membrane, said portion being reintroduced to a patient during a patient's subsequent inhalation.

4. An apparatus according to claim 1 wherein said second opening in said membrane being in communication with a second source of said pressurized gas.

5. An apparatus according to claim 4 wherein said third opening is adjacent said second opening.

6. An apparatus for delivering a highly concentrated mixture to a patient comprising:

a collapsible membrane defining a chamber therein, said membrane further defining a first opening and a second opening in communication with said chamber;

a mask defining an enclosure having a first passageway in communication with said first opening;

a nebulizer having a body defining a reservoir for holding a liquid therein, said body including an inlet orifice and an outlet orifice, said outlet orifice in communication with said second opening;

at least two pressurized gas sources each containing a pressurized gas, at least one of said at least two pressurized gas sources in communication with said inlet orifice for providing pressurized gas to said nebulizer;

at least another one of said at least two pressurized gas sources providing a pressurized gas to said chamber;

wherein when said pressurized gas from said at least one of said at least two pressurized gas sources enters said nebulizer, said pressurized gas mixes to form a mixture with said liquid inside said reservoir of said nebulizer, wherein said mixture is forced from said reservoir to said chamber where said mixture further mixes with said pressurized gas from said at least another one of said at least two pressurized gas sources before freely communicating in either direction between said chamber and said mask.

7. An apparatus according to claim 6 wherein said pressurized gas provided by said at least one of said at least two pressurized gas sources is different from said pressurized gas provided by said at least another one of said at least two pressurized gas sources.

8. An apparatus according to claim 7 wherein said pressurized gas provided by said at least another one of said at least two pressurized gas sources is helium.

9. An apparatus for delivering a highly concentrated mixture to a patient comprising:

a collapsible membrane defining a chamber therein, said membrane further defining a first opening and a second opening;

a mask including an enclosure defining a first passageway in communication with said first opening, said enclosure further defining at least one second passageway for permitting a patient to exhale into atmosphere;

a nebulizer having a body defining a reservoir for holding a liquid therein, said body having an inlet orifice formed therein, said body further having an outlet orifice in communication with said second opening;

at least two pressurized gas sources each containing a pressurized gas, at least one of said at least two pressurized gas sources in communication with said inlet orifice for providing pressurized gas to said nebulizer;

at least another one of said at least two pressurized gas sources providing a pressurized gas to said chamber;

wherein when said pressurized gas from said at least one of said at least two pressurized gas sources enters said nebulizer, said pressurized gas mixes to form a mixture with said liquid inside said reservoir of said nebulizer, wherein said mixture is forced from said reservoir to said chamber where said mixture further mixes with said pressurized gas from said at least another one of said at least two pressurized gas sources before freely communicating in either direction between said chamber and said mask, wherein a portion of a patient's exhalation returns to said membrane, said portion being reintroduced to a patient during a patient's subsequent inhalation.

10. A method for operating an apparatus for delivering a highly concentrated mixture to a patient, the steps comprising:

a) providing a device including a collapsible membrane defining a chamber therein, the membrane further defining a first opening and a second opening in communication with the chamber; a mask defining an enclosure having a first passageway in communication with the first opening; a nebulizer having a body defining a reservoir for holding a liquid therein, the body including an inlet orifice and an outlet orifice, the outlet orifice in communication with the second opening of the membrane; a pressurized gas source containing a pressurized gas, the pressurized gas source in communication with the inlet orifice for providing the pressurized gas to the nebulizer; wherein when the pressurized gas from the pressurized gas source enters the nebulizer, the pressurized gas mixes to form a mixture with the liquid inside the reservoir of the nebulizer, wherein the mixture is forced from the reservoir to the chamber before freely communicating in either direction between the chamber and the mask;

b) opening the pressurized gas source so that it is in communication with the inlet orifice;

c) securing the mask about a patient's face; and d) returning a portion of a patient's exhalation to the membrane, the portion being reintroduced to a patient during a patient's subsequent inhalation.

11. A method for operating an apparatus for delivering a highly concentrated mixture to a patient, the steps comprising:

a) providing a device including a collapsible membrane defining a chamber therein, the membrane further defining a first opening and a second opening in communication with the chamber; a mask defining an enclosure having a first passageway in communication with the first opening; a nebulizer having a body defining a reservoir for holding a liquid therein, the body including an inlet orifice and an outlet orifice, the outlet orifice in communication with the second opening; at least two pressurized gas sources each containing a pressurized gas, at least one of the at least two pressurized gas sources in communication with the inlet orifice for providing pressurized gas to said nebulizer; at least another one of the at least two pressurized gas sources providing a pressurized gas to the chamber; wherein when said pressurized gas from the at least one of the at least two pressurized gas sources enters said nebulizer, the pressurized gas mixes to form a mixture with the liquid inside the reservoir of the nebulizer, wherein the mixture is forced from the reservoir to the chamber where the mixture further mixes with the pressurized gas from the at least another one of the at least two pressurized gas sources before freely communicating in either direction between the chamber and the mask;

b) opening the pressurized gas sources so that they are in communication with the nebulizer and the membrane;

c) securing the mask about a patient's face; and d) returning a portion of a patient's exhalation to the membrane, the portion being reintroduced to a patient during a patient's subsequent inhalation.

* * * * *